United States Patent
McVenes et al.

(10) Patent No.: US 6,966,322 B2
(45) Date of Patent: Nov. 22, 2005

(54) ENHANCED CHRONIC LEAD REMOVAL

(75) Inventors: Rick D. McVenes, Isanti, MN (US); Kenneth B. Stokes, Anoka, MN (US); Michael J. Ebert, Fridley, MN (US); James M. Anderson, Cleveland, OH (US)

(73) Assignee: Medtronic, Inc., Minneapolis, MN (US)

( * ) Notice: Subject to any disclaimer, the term of this patent is extended or adjusted under 35 U.S.C. 154(b) by 526 days.

(21) Appl. No.: 10/126,747

(22) Filed: Apr. 19, 2002

(65) Prior Publication Data

US 2003/0028224 A1 Feb. 6, 2003

Related U.S. Application Data

(60) Provisional application No. 60/285,187, filed on Apr. 20, 2001.

(51) Int. Cl.$^7$ ................................................ A61B 17/88
(52) U.S. Cl. ........................ 128/899; 607/36; 607/99; 606/108; 128/898
(58) Field of Search .................. 607/36, 63, 96, 607/98, 99, 104, 105, 116, 119, 121, 122, 126, 153; 128/898, 899; 606/108, 21, 22, 24, 27

(56) References Cited

U.S. PATENT DOCUMENTS

| | | | |
|---|---|---|---|
| 4,861,830 A | 8/1989 | Ward, Jr. ................ 525/92 |
| 4,934,049 A | 6/1990 | Kiekhafer et al. ......... 29/883 |
| 4,963,595 A | 10/1990 | Ward et al. ............. 525/415 |
| 4,968,533 A | 11/1990 | Gsell .................... 427/245 |
| 5,090,422 A | 2/1992 | Dahl et al. .............. 128/784 |
| 5,589,563 A | 12/1996 | Ward et al. ............. 528/44 |
| 5,609,622 A | 3/1997 | Soukup et al. ........... 607/122 |
| 5,895,563 A | 4/1999 | Muranushi .............. 205/210 |
| 5,902,329 A * | 5/1999 | Hoffmann et al. ........ 607/121 |
| 5,939,576 A | 8/1999 | Lichtenhan et al. ...... 556/460 |
| 6,671,561 B1 * | 12/2003 | Moaddeb ................ 607/120 |

FOREIGN PATENT DOCUMENTS

| | | | | |
|---|---|---|---|---|
| EP | 0474617 | 3/1992 | ........ | B01D/67/00 |
| JP | WO 01/07097 | 2/2001 | ........ | A61L/33/06 |
| WO | WO 99/24174 | 5/1999 | ........ | B05D/5/00 |

OTHER PUBLICATIONS

Christenson et al., "Inhibition of In Vivo Inflammatory Cell Adhesion by Surface Modifying End Groups", *Society for Biomaterials 27$^{th}$ Annual Meeting Transactions*, Apr. 2–29, 2001, pp. 501, Society for BioMaterials, USA.

(Continued)

*Primary Examiner*—Kennedy Schaetzle
(74) *Attorney, Agent, or Firm*—Girma Wolde-Michael; Paul H. McDowall; Michael C. Soldner

(57) ABSTRACT

An implantable medical device, perhaps a pacemaker lead, has a medical unit and a casing at least partially enclosing the medical unit. The casing is formed of a base polymer having surface modifying pendant groups formed of an acrylamide polymer or an acrylamide copolymer, perhaps polyisopropyl acrylamide. The base polymer may be a polyurethane, polyimide, fluoropolymer or polyolefin, for example.

8 Claims, 5 Drawing Sheets

OTHER PUBLICATIONS

Patel et al., "Effects of SME Surface Chemistry and Shear Stress on Bacterial and Neutrophil Adhesion", *Society for BioMaterials, 27th Annual Meeting Transactions*, Apr. 2–29, 2001, Society for BioMaterials 27th Annual Meeting Transactions, Apr. 2–29, 2001, Society for Biomaterials, USA.

Jones et al., "Effects of Polurethanes with SMEs on Fibroblast Adhesion and Proliferation and Monocyte and Macrophage Adhesion", *Society for Biomaterials 27th Annual Meeting Transactions*, Apr. 2–29, 2001, Society for BioMaterials, USA.

Ebert, M. et al., "Polyurethane Lead Insulation Improvements using Surface Modifying Endgroups", *Society for Biomaterials 27th Annual Meeting Transactions*, Apr. 2–29, 2001, Society for BioMaterials, USA.

McVenes et al., "Modifying Cell Adhesion to Polyurethane Lead Insulation", *Society for Biomaterials 27th Annual Meeting Transactions*, Apr. 2–29, 2001, Society for BioMaterials, USA.

McVenes et al., Abstract of "Modifying Cell Adhesion to Polyurethane Lead Insulation", *Society for Biomaterials 27th Annual Meeting Transactions*, Apr. 2–29, 2001, Society for BioMaterials, USA.

Hopkins et al., "Chiral Polyolefins Bearing Amino Acids", *Macromolecules 2001*, vol. 34, pp. 7920–7922, American Chemical Society.

O'Donnell et al., "'Perfect Comb' ADMET Graft Copolymers", *Macromolecules 2001*, vol. 34, pp. 6845–6849, American Chemical Society.

* cited by examiner

ENHANCED CHRONIC LEAD REMOVAL

CROSS REFERENCE TO RELATED APPLICATIONS

This application is based on and hereby claims priority to U.S. Provisional Application No. 60/285,187 filed on Apr. 20, 2001, the contents of which are hereby incorporated by reference.

INCORPORATION BY REFERENCE

This application incorporates by reference the contents of U.S. Pat. No. 5,589,563 to Ward et al., issued Dec. 31, 1996.

BACKGROUND OF THE INVENTION

It has become common to treat many diseases using implantable medical devices (IMDS) that are chronically implanted within the body of a patient. Examples of such medical devices include pacemakers, defibrillators, drug-delivery devices, and electro-stimulators for stimulating nerves, muscles, and other tissue.

One problem associated with the chronic implantation of IMDs involves the growth of fibrous tissue around the device. When a foreign object such as an IMD is introduced into a patient's body, the body's auto-immune system forms a collagen capsule around the foreign object. This capsule, which has fibrous tissue, attaches to the IMD in a manner that prevents easy extraction of the device. This makes it difficult to replace or re-locate a medical device after it has been in the body any significant amount of time. This problem is particularly prevalent when dealing with implantable medical leads.

Implantable medical leads have many uses. For example, leads carrying electrodes and other sensors are often positioned within a chamber of the heart or in the associated vasculature. These leads, which are coupled at one end to an IMD, may be used to delivery electrical stimulation to cardiac tissue, and/or to sense physiological signals. Leads may also be utilized to deliver medication to the body as controlled by a drug delivery device.

As noted above, the formation of fibrous tissue surrounding a medical lead results in problems when the lead is to be replaced or re-located. The problems are exasperated by the formation of small micro cracks in the surface of the lead body. These cracks result when leukocytes release oxygen-free radicals causing an autoxidation reaction at the lead's surface. The small crevices create additional surface area and spaces within which fibrous tissue can bond, making chronic lead extraction even more difficult.

Many methods have been devised in attempt to prevent the bonding of collagenous capsule tissue to the surface of implantable leads. If such bonding could be prevented, the extraction of chronically-implanted leads would be greatly simplified. One manner of attempting to prevent tissue in-growth is disclosed in U.S. Pat. No. 5,609,622, which describes coating a lead with a porous Polytetrafluoroethylene (PTFE) layer such as may be formed of expanded PTFE (e-PTFE), and which has a pore size of less than 10 microns or smaller so that the pore size is very small, and tissue in-growth is prevented.

Other methods of preventing tissue in-growth are directed more specifically at eliminating the formation of tissue around the electrode structures carried on some lead bodies. One mechanism disclosed in U.S. Pat. No. 4,934,049 issued to Kiekhafer et al. involves injecting silicone rubber into the spaces between the individual coils of an electrode structure. The resulting thin coating of silicone rubber surrounding the exterior of the electrode coils minimizes tissue in-growth between the filars of the coils, while leaving a portion of the coils exposed to deliver electrical stimulation to a patient.

Another approach to preventing tissue in-growth is disclosed in U.S. Pat. No. 5,090,422, which describes the use of biocompatible porous materials such as woven, porous polyurethane and porous polytetrafluoroethylene that may be used to cover an electrode or lead surface. The material is insulative when dry, but becomes conductive when bodily fluids penetrate the pores of the material. The porous covering has an adequately small pore size and fibril length to preclude substantial tissue in-growth Although the foregoing mechanisms have been developed in attempt to prevent collagen formation with the surface of an IMD, problems still remain. The foregoing mechanisms are not entirely effective in preventing collagen attachment within the small micro cracks formed in the surface of leads, for example. Moreover, the foregoing mechanisms does not address the problems associated with autoxidation caused by the oxygen-free radicals. Therefore, what is needed is an improved system and method to prevent tissue in-growth in the surface of a chronically-implanted medical device.

SUMMARY OF THE INVENTION

These and other objects are accomplished by providing in an improved implantable medical device and methods of forming, the implanting and extracting implantable medical device. According to a first aspect of the invention, an implantable medical device, perhaps a pacemaker lead, has a medical unit and a casing at least partially enclosing the medical unit. The casing is formed of a base polymer having surface modifying pendant groups formed of an acrylamide polymer or an acrylamide copolymer, perhaps polyisopropyl acrylamide. The base polymer may be a polyurethane, polyimide, fluoropolymer or polyolefin, for example.

The pendant groups can be attached to a back bone of the base polymer or attached as surface modifying end groups covalently bonded to the base polymer.

For the end attachment, the base polymer may having surface modifying end groups formed of the acrylamide polymer or acrylamide copolymer may have a surface tension that differs by at least one dyne/cm from the surface tension of an otherwise identical polymer having diethylamino end groups. An outer layer may be formed on the casing and covalently bonded to the surface modifying end groups.

The medical unit may have a shell having an outer surface. In this case, the casing is formed on the outer surface of the shell.

According to a second aspect of the invention, a method of implanting a removable medical device is provided. The method involves implanting in a patient a medical unit having a casing formed of a base polymer having surface modifying pendant groups and allowing the surface modifying pendant groups to form a hydrogel within the patient. The hydrogel may have a water content of at least 10 weight %.

According to a third aspect of the invention, an implantable medical device has a medical unit and a casing at least partially enclosing the medical unit. The casing is formed of a base polymer having cross linked surface modifying end groups. Silicone may be used as the base polymer. In this case, the surface modifying end groups may be formed from a silica free silicone and contain vinyl functionality to promote cross-linking.

According to a fourth aspect of the invention a method of forming an implantable medical device is provided. The method involves forming a medical unit and forming a casing at least partially enclosing the medical unit. The casing is formed of a base polymer having surface modifying pendant groups. After forming the casing, a polymeric outer layer is formed on the casing by covalently bonding the polymeric material to the surface modifying pendant groups.

The outer layer may be formed of a polymeric material different from the base polymer forming the casing.

According to a fifth aspect of the invention, an implantable medical device is provided, which device has a medical unit, a casing at least partially enclosing the medical unit, and a thermally active device. The casing is formed of a base polymer having surface modifying pendant groups. The thermally active device may be an electric heating element provided within the implantable medical device or lumen located within the implantable medical device for receiving heated or chilled fluids.

According to a fifth aspect of the invention, the temperature of an implanted medical device is changed, perhaps through the thermally active device and then the implanted medical device is extracted. Heating the implanted medical device to a temperature of at least 40° C. may denature collagen surrounding the implanted medical device. If the surface modifying end groups of the casing form a hydrogel within a patient, then cooling the implanted medical device to a temperature of at least 30° C. may change the water content of the hydrogel. An implantable medical device, perhaps a pacemaker lead, has a medical unit and a casing at least partially enclosing the medical unit. The casing is formed of a base polymer having surface modifying pendant groups formed of an acrylamide polymer or an acrylamide copolymer, perhaps polyisopropyl acrylamide. The base polymer may be a polyurethane, polyimide, fluoropolymer or polyolefin, for example.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE EMBODIMENTS

Figure 1:
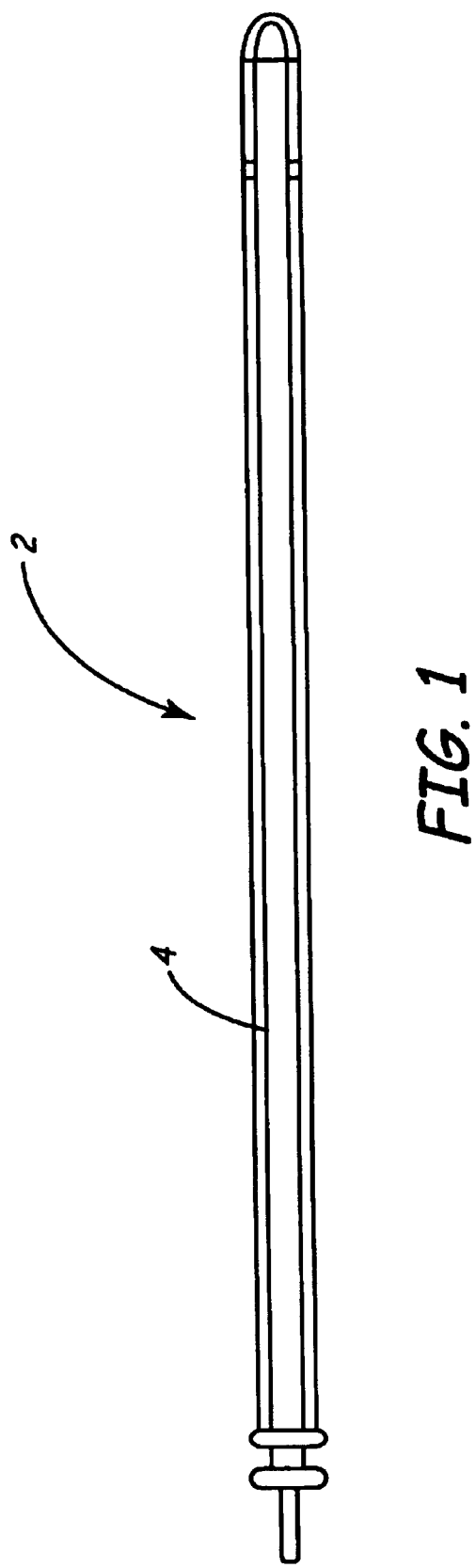
FIG. 1 is a cut away side view of a medical lead coated with a polymer having surface modifying end groups.

It has been discovered that coating a surface of an IMD with a polymer including surface modifying end (SME) groups protects the surface of the IMD in several ways. First, some SMEs operate to separate leukocytes from the lead's surface. As discussed above, leukocytes are structures within the body that release oxygen-free radicals when a foreign object is introduced into the body. These radicals react with the surface of an IMD causing autoxidation and formation of micro cracks. The SMEs may react with the free radicals, preventing the radicals from combining with the lead's surface, and therefore preventing this cracking from occurring. When surface cracking is prevented, it is more difficult for tissue to adhere to the surface of the IMD. Thus, the lead can be slid from a patient for removal from encapsulated tissue with relatively little difficulty. Even a very thin molecular monolayer of polyurethane having SME groups will operate in this manner.

Some SMEs such as polyethylene oxide allow oxidation of the IMD surface while acting as a barrier to $\alpha_2$-macroglobulin, which works to produce cracks in the IMD surface.

Other SMEs that may be employed to prevent tissue in-growth include methyl phosphoryl choline and polyisopropyl acrylamide. In particular, polyisopropyl acrylamide may be used as an SME alone, or as an attachment primer for the covalent bonding of a thicker layer of the same polymer. The polymer forms a hydrogel composed of up to 90% water (depending on the formulation), which makes lead removal much less difficult.

The hydrogels are not restricted to polyisopropyl acrylamide. Many other acrylamides and acrylamide copolymers will form a hydrogel when they come into contact with water. An IMD having a surface coating with SMEs formed from an acrylamide polymer or an acrylamide copolymer is dry when transported and implanted. After implanted, the acrylamide polymer or acrylamide copolymer absorbs body fluids to form a hydrogel. The hydrogel may contain at least 10 wt. % water, more particularly at least 50 wt. % water, and still more particularly at least 70 wt. % water.

The surface modifying groups are not necessarily attached to the polymer as end groups. The surface modifying agents may also be attached to the polymer back bone. The term "surface modifying pendant group" is used herein to generically describe surface modifying agents attached as end groups and attached to the back bone.

To attach a surface modifying agent to the back bone of a polymer, the agent can be grafted or branched onto the polymer using ADMET chemistry, which is described in Wagener et al. "Chirel Polyolefins Bearing Amino Acids", *Macromolecules*, 34, 7920–7922 (2001) and Wagener et al., "Perfect Comb ADMET Grafted Copolymers", *Macromolecules*, 34, 6845–6849 (2001). ADMET chemistry requires double bonds within the polymer back bone. The surface modifying agent attaches to the double bonds. Olefin metathesis chemistry can also be used to attach surface modifying agents to the back bone of the polymer. This process uses catalysts including molybdenum, tungsten, rhenium, ruthenium and alloys thereof. Olefin metathesis chemistry is described in U.S. Pat. No. 5,939,576 to Lichtenhan et al., for example.

It has further been discovered that temperature and pH sensitive formulations of SMEs have unique properties. For example, changing temperature from between 25 and 40° C. can reverse surface energy, causing cells to lose adhesion and detach from the surface of the lead. Changes in temperature further modify the water concentration of an SME hydrogel, resulting in swelling or shrinking of the hydrogel layer. For example, cooling of a lead is generally found to cause the surface to become hydrophilic and hydrated, making it more difficult for cells to adhere to the surface. The IMD or lead may be cooled to at least 30° C., more particularly to at least 25° C., and still more particularly to at least 20° C.

According to another aspect of the invention, it has been observed that the SME polyethylene oxide and fluorocarbon SMEs reduce adhesion of cells such as fibroblasts, making lead extraction easier to accomplish. This effect is enhanced when these types of SMEs are cooled, which causes any fibroblasts that did adhere to the SME to be released. For example, the cooling may be performed to 10° C. for one hour.

According to another aspect of the current invention, it has been discovered that heating an IMD or lead will denature a collagen capsule, facilitating lead extraction and/or removal. The IMD or lead may be heated to at least 40° C., more particularly to at least 45° C., and still more particularly to at least 50° C.

Heating and cooling of a lead may be performed by circulating water within one or more lumens provided for this purpose. Alternatively, heating may be performed by providing heating elements formed of conductive members that are embedded within the walls of the lead. Directing current through the heating elements causes the temperature of the lead body to increase.

In a manner similar to that discussed above with respect to temperature changes, some SMEs are responsive to changes in pH. When predetermined pH changes occur, the fibroblasts will not adhere to the SME surface, and lead removal can be much more easily accomplished. This is important because one of the major reasons to remove chronically embedded leads is infection. Infections generally produce a pH change of the type needed to facilitate chronic lead removal.

Other types of SMEs prevent free radicals from reaching the surface of the lead. For example, fluorocarbon and silicone produce a non-reactive surface barrier, forcing the free radicals to react with something other than the polymer, thereby protecting the surface of the lead. Yet other SMEs operate to provide a barrier to crack-producing catalysts such as ceruloplasmin and $\alpha_2$-macroglobulin.

Inhibition of calcification in bioprosthetic heart valves using sustained local release of calcium and sodium diphosphonates has been reported. However, phosphonates released systemically can have adverse effects on overall growth, bone development and calcium metabolism. Immobilization of ethanehydroxydiphosphonate within a bioprosthetic heart valve as the poorly soluble $Ca^{2+}$ salt inhibits calcification at drug levels insufficient to produce side effects. However, rapid time-dependent efflux of the phosphonate from the pericardial tissue limited its usefulness in long-term heart valve replacements. The use of diphosphonates as SMEs or attached to SMEs such as PEO, hydrocarbon, silicone or fluorocarbon, etc. will control mineralization of silicone rubber pacemaker leads, enhancing their chronic extractability.

In one embodiment, a casing formed of a polymer having SMEs is extruded over an outer surface of a shell for the IMD, perhaps a lead. That is, two outer bodies (shell and casing) are provided instead of one (casing). This produces a very smooth surface that is resistant to abrasions and cracking during the implanted-life of the lead. The outer shell may be formed of any conventional material used to enclose IMDs.

Another problem associated with IMDs generally, and more in particular to implantable leads, involves silicon rubber devices and the use of silica at or near the surface. The use of silica at or near the surface of silicone rubber leads makes the surface tacky, resulting in a high friction coefficient when the lead is advanced within the body. To reduce this effect, the lead surface may be plasma treated to change the chemical and physical characteristics of the surface. These treatments cause the lead to be more lubricious when wet, but also promote tissue in-growth by imparting additional micro cracks in the lead surface. One aspect of the invention addresses this problem by providing a very smooth silica-free silicone surface coating on the surface of a silicone lead body. The surface coating is designed with cross-link density to be tack-free when dry, to provide implant lubricity, and to further enhance chronic lead extraction.

FIG. 1 is a side cutaway view of a medical lead according to one aspect of the invention. The lead includes an elongated lead body 2, which is covered over at least a portion of it's surface with a coating 4. The coating 4 is formed of a polymer having SMEs. Although a lead is shown for discussion purposes, it will be understood that the surface of other IMDs may be used, including surfaces of catheters, leads, any chronically-implanted device, or any surface of any IMD.

EXAMPLES

Fibroblast adhesion to, and detachment from, temperature responsive polymers and modified biomaterial surfaces were investigated in a time and temperature dependent manner. The biomaterial surfaces studied were Corethane 80A, Pellethane 80A clone (P80AC), P80AC with a surface modified end group (SME) of polyethylene oxide (PEO), and P80AC with a fluorocarbon SME. Fibroblast adhesion and detachment were examined using tissue culture polystyrene (TCPS) as a control. A temperature responsive surface (TRS), created by grafting chains of Posy (N-isopropylacrylamide) (NIPAAm) onto TCPS was also investigated. Here, human dermal fibroblast adhesion on these surfaces is examined at 37° C. Also, fibroblast proliferation is evaluated over a 7-day period at days 1, 4, and 7. Finally, fibroblast detachment from the biomedical polymers using trypsin or by cooling is studied. Trypsin was used to remove all of the fibroblasts from each surface at 37° C. Cooling the TRS surfaces to 10° C. for 60 minutes induced a change in the surface chemistry (hydrophobic to hydrophilic 1), which promoted either fibroblast adhesion or fibroblast detachment. At 37° C. (fibroblast culture temperature), the TRS surface was hydrophobic which promoted fibroblast adhesion. However, after cooling, the surface became hydrophilic. By using both trypsin at 37° C., and cooling to 10° C., we were able to compare the detachment of fibroblasts with each material.

At 37° C., fibroblasts adhered to and proliferated on TCPS, P80AC, Corethane 80A, and TRS over the 7-day period. Fibroblast adhesion was observed on TCPS the most, while the most proliferation occurred on the TRS. There was limited adhesion, proliferation, and detachment observed on both Pellethane materials with SMEs. These results suggest that fluorocarbon and PEO SMEs on pellethane surfaces inhibit fibroblast adhesion and proliferation. When cooled to 10° C., the TRS released the fibroblasts in a temperature dependent fashion at days 1 and 4, but not at day 7. Adherent fibroblasts on the biomedical polymers and TCPS detached to a much lower extent then adherent fibroblasts on TRS. This indicates that cell detachment was dependent not on temperature but rather on temperature-induced surface changes.

Poly(N-isopropylacrylamide), a temperature responsive surface (TRS) can detach cells without enzymatic treatment.

The lower critical solution temperature (LCST) of the NIPAAm used to make TRS is 32° C. Above 32° C., TRS is hydrophobic and dehydrated, while at temperatures below 32° C., it is hydrophilic and hydrated. Cell adhesion is greater on hydrophobic surfaces rather than hydrophilic surfaces. Cells adhere to TRS at 37° C., but detach upon cooling the surface to 10° C. hydrated.

Materials and Methods

Materials

The materials used in this study are shown below in which "Pellethane 80A clone" represents an aromatic polyether polyurethane with a Shore A hardness of 80A, and Corethane 80A" represents an aromatic polycarbonate polyurethane with a Shore A hardness of 80A.

TABLE I

Preparation of Materials for Culturing

| Material | Name |
| --- | --- |
| TCPS | Tissue Culture Polystyrene |
| TRS | Temperature Response Surface (NIPAMM) |
| A | Pellethane 80A clone |
| B | Pellethane 80A clone with 6% Fluorocarbon |
| C | Pellethane 80A clone with 6% PEO SME |
| D | Corethane 80A |

All of the polyurethanes were received as sheets. These sheets were punched into 15 mm diameter disks using a stainless steel punch. Punched disks were rinsed in 10% ethanol and rinsed in ultrapure water, and then air-dried prior to use. When ready to use these materials, they were sonicated in 100% ethyl alcohol for 5 minutes. Silicone tubing (Cole-Parmer, Vernon Hills, Ill.) was cut into small sections approximately ⅓ inch, sonicated using the same process as the materials and autoclaved for one hour. Under sterile conditions in a laminar flow hood, the materials were inserted into 24-well plates and then secured by the silicone rings.

Contact Angles

Advancing water contact angle measurements were used to analyze the hydrophobicity/hydrophilicity of the materials. The contact angle was measured on all materials using a goniometer (Edmund Scientific Co. Barrington, N.J.). These measurements were taken at 24° C. (room temperature) and at 4° C.

Cells

Cell Line

Human foreskin fibroblasts (NIA Cell Culture Repository Camden, N.J.) were used in their 6th passage for this study. The fibroblasts media was aspirated and rinsed using Dulbecco's Phosphate Buffer Saline (DPBS) (Gibco BRL Gaithersburg, Md.). The fibroblasts were retrieved using a trypsin solution containing 0.5 mg of trypsin per 1 ml of Hank's Balanced Salt Solution with 3 mM $Na_2EDTA$ (Gibco BRL Gaithersburg, Md.). The enzymatic treatment was terminated using an equal amount of warmed Dulbecco's Modified Eagles Medium (DMEM) (Gibco BRL Gaithersburg, Md.) with 5% heat inactivated fetal bovine serum (FBS) (Hyclone Logan, Utah). The fibroblasts were centrifuged from the solution and resuspended in fresh DMEM culture media with 5% FBS. After plating, the unused fibroblasts were passed into a new flask and refed once a week with the same culturing media.

Cell Culture

Figure 2:
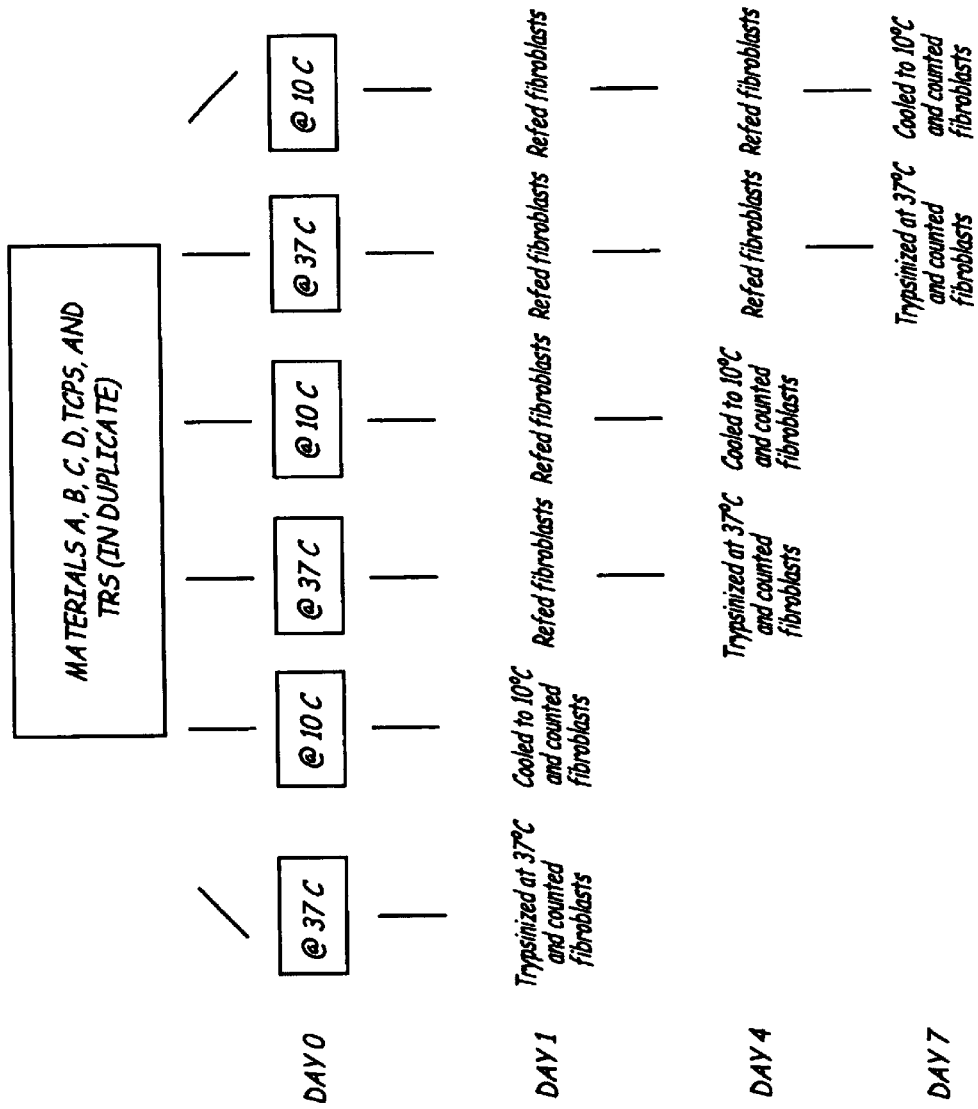
FIG. 2 is a schematic representation of a test process performed on fibroblast cultures for different materials.

The detached fibroblasts were plated to the materials in each well at a plating density of 15,000 fibroblasts per well under sterile conditions. The fibroblasts were incubated at 37° C. in humidified conditions of 5% $CO_2$. Cultures were terminated at days 1, 4, and 7. Remaining cultures at each time point were refed fresh, DMEM culture media with 5% FBS. The schematic representation of the process performed on each culture is shown in FIG. 2.

Detachment Using Trypsin

At days 1, 4, and 7, non-adherent fibroblasts were aspirated from the wells and rinsed with DPBS for 1 minute. Using the trypsin solution, all adherent fibroblasts were removed from the surface. The fibroblasts were incubated in this solution for 2½ minutes. Upon trypsinizing the cells, all surfaces were checked using light microscopy for total fibroblast removal. Then, the cells were suspended in Isoton saline (Fisher Scientific Pittsburgh, Pa.) by gently pipetting. Samples were counted using the Coulter Counter ZM (Coulter Hialeah, Fla.).

Detachment Using Cooling

The fibroblasts were gradually detached from the wells after incubation by cooling the surfaces and fibroblasts to 10° C. for 1 hour. The detached cells were pipetted and suspended in Isoton saline. Then, the detached cells were counted using the Coulter Counter. Cells were detached by cooling at days 1, 4, and 7.

Cell Subculture

In order to determine vitality, fibroblasts detached by cooling were replated to TCPS in a 24-well plate. The fibroblasts were cultured for 4 days in DMEM culture media with 5% fatal bovine serum.

Material Analysis

For visual analysis, all fibroblast were fixed by incubating them in 100% methanol for 5 minutes then allowing the surfaces to air-dry. Upon drying, the surfaces were rinsed 2–3 times with a phosphated buffer solution and then stained. To stain the samples, the surfaces were incubated in a May-Grunwald dye for 1 minute, which was aspirated and rinsed using PBS. Then these surfaces were incubated in a Giemsa stain for 5 minutes, aspirated, rinsed two times with distilled water, and allowed to air dry. These samples were then examined using light microscopy for differences in cell morphology and adhesion at all time points and temperatures Results Contact Angle Analysis Advancing dynamic water contact angles of the materials used in this study are shown in Table II.

TABLE II

Dynamic Water Contact Angles of Biomaterials*

| Material | Contact Angle at 22° C. | Contact Angle at 4° C. |
| --- | --- | --- |
| TCPS | 77 ± 0.8 | 75 ± 3.2 |
| TRS | 56 ± 6.5 | 38 ± 3.7 |
| A | 65 ± 3.3 | 71 ± 6.4 |
| B | 89 ± 2.6 | 93 ± 4.4 |
| C | 73 ± 2.2 | 75 ± 3.6 |
| D | 71 ± 4.7 | 76 ± 5.8 |

*Values given as mean ±SEM; n = 3 for each material.

At 22° C. (room temperature), all of the materials displayed a hydrophobic nature. The addition of the surface modified end-groups of PEO and fluorocarbon to material A caused an increase in the material's hydrophobicity from 65°±3.3° to 89°±2.6° and 73°±2.2°. The addition of the fluorocarbon SME to material A caused the greatest increase in hydrophobicity. Chains of NIPAAm were grafted to polystyrene surfaces to create temperature responsive surface as described by N. Yamada. Grafting the chains of NIPAAm caused a decrease in the hydrophobicity compared to the TCPS.

Upon cooling to 4° C., materials A, B, C, D, and TCPS maintained their hydrophobic state. However, the water contact angle of TRS significantly decreased from 56°±6.5° to 38°±3.7°. This indicates that the surface properties of the material changed from hydrophobic to hydrophilic with cooling.

Figure 3:
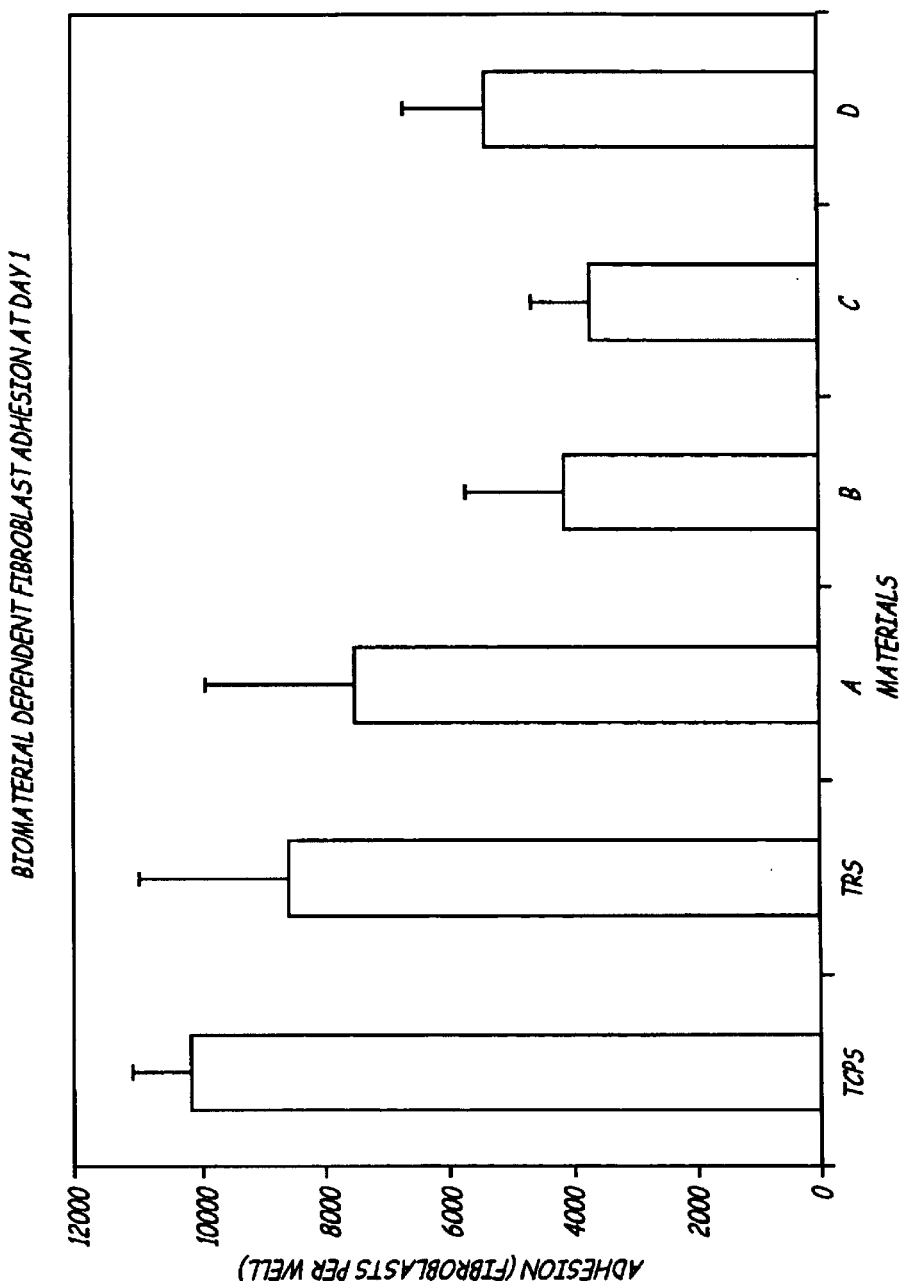
FIG. 3 is a graph showing initial fibroblast adhesion on different materials.

Fibroblast Adhesion At day 1, the adherent fibroblasts were measured based on the removal of all adherent cells using trypsin. FIG. 3 shows the initial fibroblast adhesion at 37° C. TCPS and TRS had the greatest initial fibroblast adhesion. TCPS had surface properties that allowed the most fibroblast adhesion compared to the other tested surfaces. This effect was decreased by the addition of NIPAAm. Initial fibroblast adhesion was lower on the materials A, B, C, and D.

Fibroblasts adhered more favorably on material A compared to material D. The SMEs caused materials B and C to be unfavorable for fibroblast adhesion, causing these surfaces to have the lowest amount of cell adhesion overall. The ranking of these materials based on fibroblast adhesion is given in Table III.

TABLE III

Various Rankings of Biomedical Polymers

| Rank of Adhesion | Rank of Proliferation |
| --- | --- |
| TCPS | TRS |
| TRS | D |
| A | A |
| D | TCPS |
| B | B |
| C | C |

Fibroblast Proliferation

Figure 4:
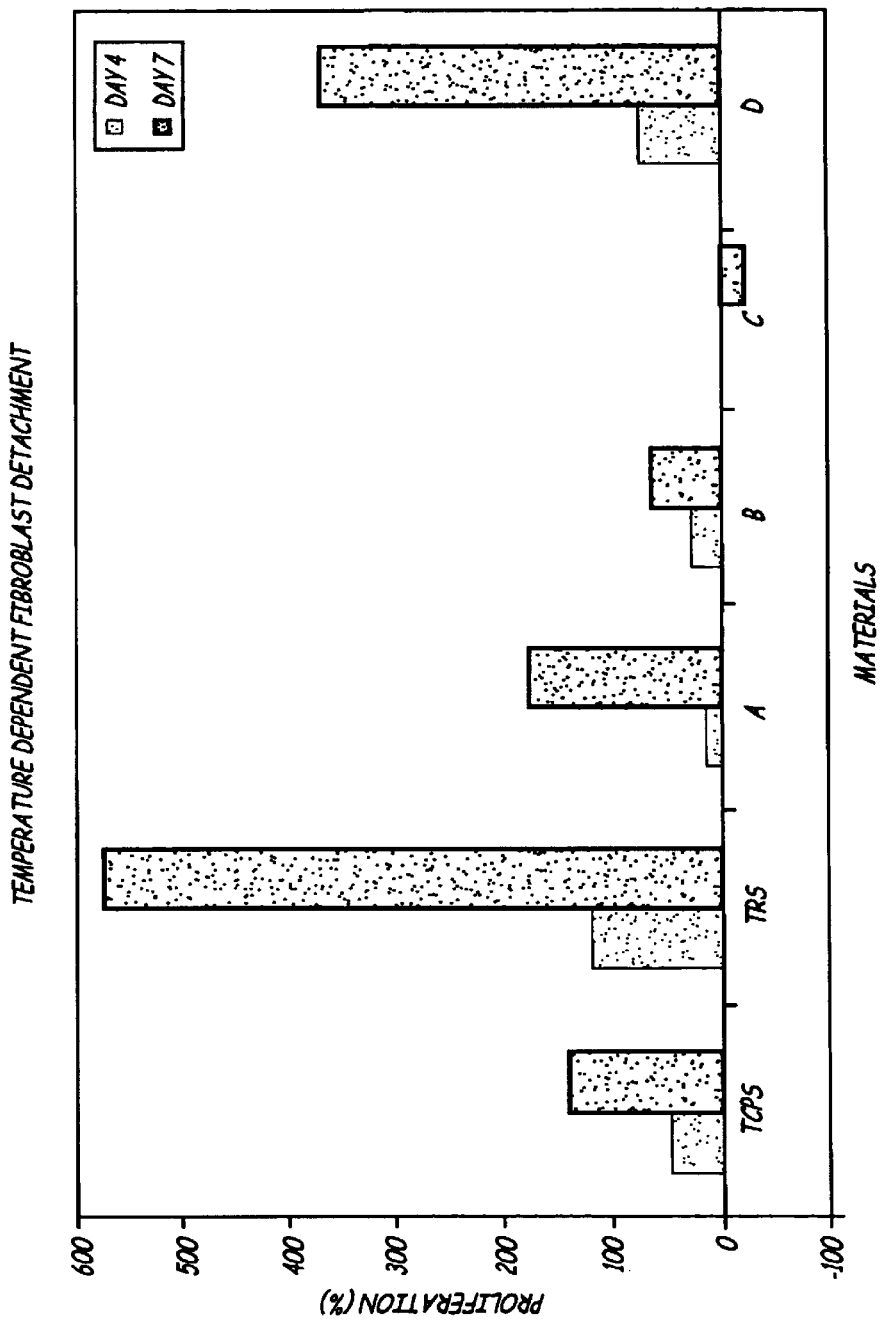
FIG. 4 is a graph showing fibroblast Proliferation at days 4 and 7 at 37° C. for the materials examined in FIGS. 2 and 3.

The fibroblasts were cultured for 4 and 7 days. By day 7, the fibroblasts had reached confluency on TCPS, TRS, and materials A and D. TRS experienced the greatest percentage of fibroblast proliferation by days 4 and 7, followed by material D. Although material A promoted fibroblast proliferation more than TCPS, materials B did not, as shown in Table 3. Material C supported very little fibroblast proliferation, by day 4, and it inhibited proliferation by day 7. FIG. 4 is a chart showing fibroblast proliferation at days 4 and 7, at 37° C., for the materials examined.

Fibroblast Detachment

Figure 5:
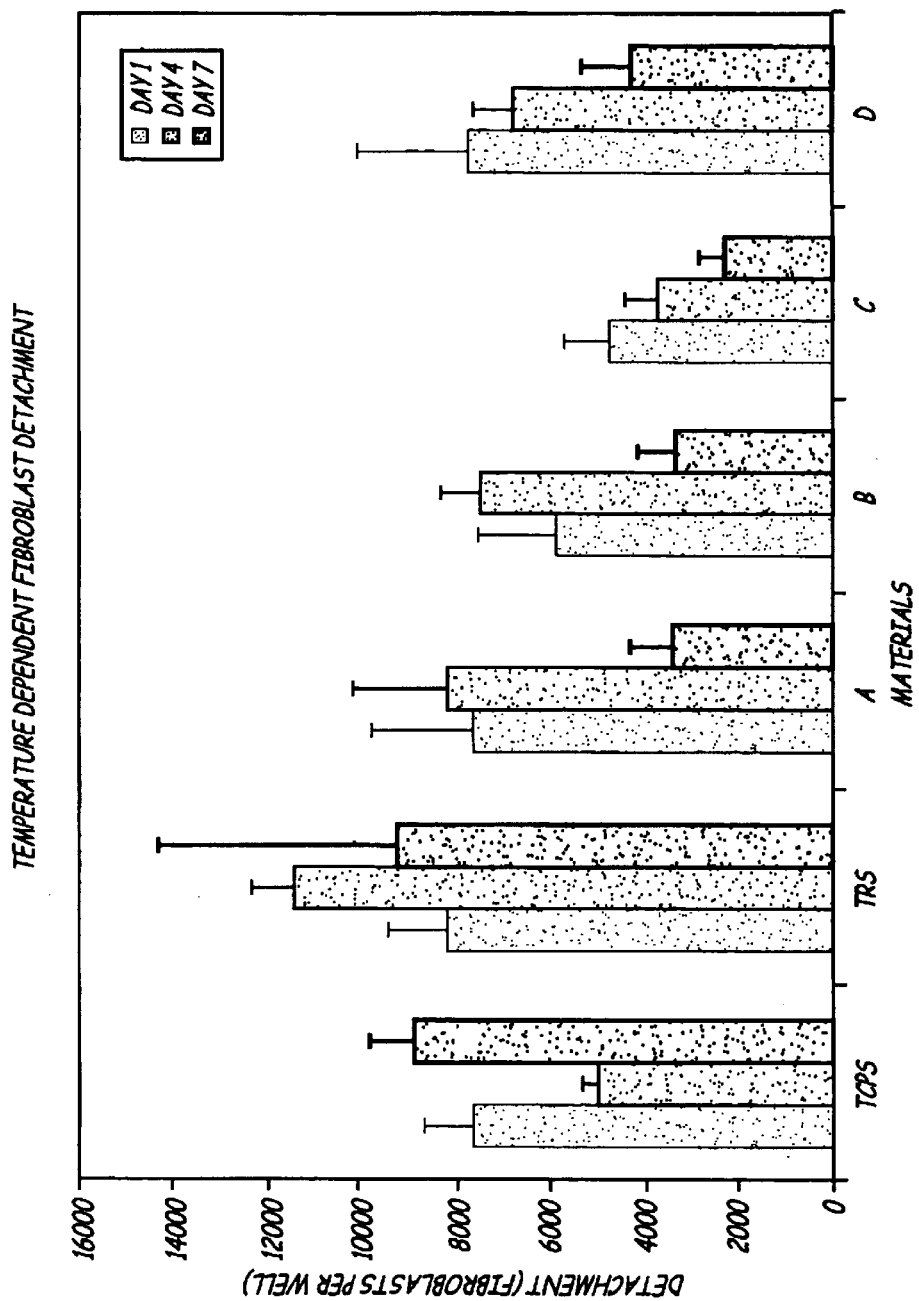
FIG. 5 is a graph showing the amount of fibroblast detachment produced by cooling to 10° C., at days 1, 4 and 7.

On days 1, 4, and 7, temperature dependent fibroblast detachment was investigated upon the cooling of the materials. Due to the proliferation experienced over the 4 and 7 day periods TRS had the most fibroblast detachment from its surface at all time points. For both TCPS and TRS, there was greater fibroblast detachment on day 7 than on day 1. However, fibroblast detachment was the least on day 7 on the biomedical surfaces, materials A, B, C, and D. Yet throughout the experiment, there was greater fibroblast detachment from material A than from materials B and C. FIG. 5 is a graph showing the amount of fibroblast detachment produced by cooling to 10° C., at days 1, 4 and 7.

Discussion

It is known that the host inflammatory response to an implant can lead to fibrous encapsulation. Increased fibroblast adhesion and proliferation cause an increases in collagen surrounding the implant that ultimately causes encapsulation. The adhesion, proliferation and detachment of fibroblasts are affected by the surface properties of the materials. Initial fibroblast adhesion was shown to be altered based on surface properties. The materials used in this study were all hydrophobic at 37° C., exhibiting a water contact angle above 56°. It has been found that hydrophobic materials support greater cell adhesion than hydrophilic materials.

Although materials B and C are more hydrophobic than material A, they were shown to have lower fibroblast adhesion. This may be due to the expressed surface properties of the fluorocarbon and PEO SMEs. Material B, the most hydrophobic material, was endcapped with fluorocarbon, which obstructs fibronectin absorption. This lack of absorbed fibronectin on material B may have inhibited fibroblast adhesion leading to decreased adhesion, when compared with material A. Material C contains PEO SME. However, PEO attracts water molecules that create a barrier to protein absorption, which in turn inhibits fibroblast adhesion.

It can be seen that fibroblast adhesion was greater on TRS than materials A, B, C, and D at 37° C. This promotion of fibroblast adhesion may be a result of TRS hydrophobicity at temperatures above 32° C., which promotes the absorption of fibronectin and increases adhesion through dehydration and compaction of NIPAAm chains. This compact state increases cell/surface interactions enabling the fibroblasts to interact more with the absorbed fibronectin.

Fibroblast proliferation will occur based on surface properties that provide the most favorable conditions for growth. These conditions are similar to those required for fibroblast adhesion, such as protein absorption, temperature, and culture medium.

Fibroblast proliferation appeared to be greater on TRS than on any other material on days 4 and 7. This is due to the favorable conditions that TRS provides for the adherent fibroblast. The hydrophobic, dehydrated state allows for increased protein absorption, which in turn may promote fibroblast proliferation.

Fibroblast detachment is a result of a change in surface properties of a material with adherent fibroblast. This change produces an environment that is no longer favorable to fibroblast adhesion. At all three time points, TRS was shown to promote fibroblast detachment at 10° C. Upon cooling, TRS undergoes numerous alterations in its surface properties. We have confirmed that at 10° C., TRS changes from hydrophobic to hydrophilic, as shown by the lowering of water contact angles shown in Table II. Along with this change, TRS also becomes hydrated causing the NIPAAm chains to enter an extended formation, which consequently, inhibits protein absorption and decreases cell/surface interactions. These conditions explain the observed increase in fibroblast detachment from TRS.

The invention has been described in detail with particular reference to preferred embodiments thereof and examples, but it will be understood that variations and modifications can be effected within the spirit and scope of the invention.

What is claimed is:

1. A method of extracting a chronically implanted medical device, comprising:

changing the temperature of an implanted medical device having a medical unit and a casing at least partially enclosing the medical unit, the casing being formed of a base polymer having surface modifying pendant groups; and extracting the implanted medical device.

2. A method according to claim 1, wherein the temperature of the implanted medical device is changed through a thermally active device included in the implanted medical device.

3. A method according to claim 1, wherein changing the temperature of the implanted medical device involves heating the implanted medical device to denature collagen surrounding the implanted medical device.

4. A method according to claim 3, wherein the implanted medical device is heated to a temperature of at least 40° C.

5. A method according to claim 1, wherein the surface modifying end groups of the casing form a hydrogel within a patient.

6. A method according to claim 5, wherein the surface modifying end groups are formed of an acrylamide polymer or an acrylamide copolymer.

7. A method according to claim 5, wherein changing the temperature of the implanted medical device involves cooling the implanted medical device to change the water content of the hydrogel.

8. A method according to claim 7, wherein the implanted medical device is cooled to a temperature of at least 30° C.

* * * * *